United States Patent [19]

Kocsis et al.

[11] 4,041,161
[45] Aug. 9, 1977

[54] CEPHALOSPORINS HAVING AN α-ACYLAMINOACETIC ACID SIDE CHAIN

[75] Inventors: Karoly Kocsis, Basel; Heinrich Peter; Hans Bickel, both of Binningen, all of Switzerland

[73] Assignee: Ciba-Geigy Corporation, Ardsley, N.Y.

[21] Appl. No.: 576,398

[22] Filed: May 9, 1975

[30] Foreign Application Priority Data

May 13, 1974  Switzerland ............... 6494/74

[51] Int. Cl.² ............. C07D 501/36; A61K 31/38; C07D 501/32; C07D 501/54
[52] U.S. Cl. .................. 424/246; 544/24; 544/25; 544/27; 544/28; 544/22
[58] Field of Search ............. 260/243 C; 424/246

[56] References Cited

U.S. PATENT DOCUMENTS

| | | | |
|---|---|---|---|
| 3,687,949 | 8/1972 | Holdrege | 260/243 C |
| 3,912,728 | 10/1975 | Crooij et al. | 260/243 C |

Primary Examiner—Nicholas S. Rizzo
Assistant Examiner—David E. Wheeler
Attorney, Agent, or Firm—Joseph G. Kolodny; John J. Maitner; Theodore O. Groeger

[57] ABSTRACT

Compounds of the formula

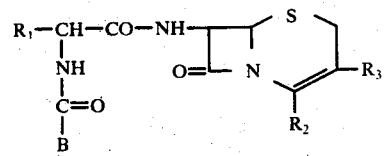

wherein $R_1$ denotes optionally substituted phenyl, thienyl, furyl or 1,4-cyclohexadienyl, $R_2$ represents a free carboxyl group or an esterified carboxyl group which can be split physiologically, $R_3$ represents hydrogen, lower akoxy or an optionally substituted methyl group and B represents an optionally substituted six-membered ring with 1 to 3 ring nitrogen atoms, which is bonded to the carbonyl group —C(=O)— by one of its carbon atoms, the nitorgen atoms of a monocyclic six-membered ring having 2 nitrogen atoms being either adjacent or separated by two ring carbon atoms, and the salts of such compounds which have a salt-forming group, including the inner salts, for example the 7β-[D(—)-α-(3,5-Dioxo-2,3,4,5-tetrahydro-1,2,4-triazine-6-carboxamido)-phenylacetamido]-cephalosporanic acid, have antibiotic activity.

6 Claims, No Drawings

CEPHALOSPORINS HAVING AN α-ACYLAMINOACETIC ACID SIDE CHAIN

The invention relates to new therapeutically valuable derivatives of 7-amino-ceph-3-em-4-carboxylic acid and their salts, processes for their manufacture and pharmaceutical preparations which contain the new compounds.

In particular, the invention relates to compounds of the formula

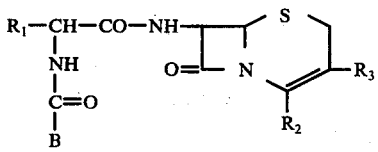

wherein $R_1$ denotes optionally substituted phenyl, thienyl, furyl or 1,4-cyclohexadienyl, $R_2$ represents a free carboxyl group or an esterified carboxyl group which can be split physiologically, $R_3$ represents hydrogen, lower alkoxy or an optionally substituted methyl group and B represents an optionally substituted six-membered ring with 1 to 3 ring nitrogen atoms which is bonded to the carbonyl group —C(=O)— by one of its carbon atoms, the nitrogen atoms of a monocyclic six-membered ring having 2 nitrogen atoms being either adjacent or separated by two ring carbon atoms, and the salts of such compounds which have a salt-forming group, including the inner salts.

Unless defined otherwise, the general expressions employed in the preceding and following text have the following meanings:

Lower alkyl is a straight-chain or branched alkyl group with 1 to 7, preferably with up to 4, carbon atoms, and denotes, for example, methyl, ethyl, propyl, isopropyl, butyl, isobutyl, tert.-butyl, pentyl, hexyl or heptyl.

Lower alkoxy is, for example, methoxy, ethoxy, propoxy, isopropoxy, butoxy, isobutoxy, tert.-butoxy, pentyloxy, hexyloxy or heptyloxy and lower alkylmercapto is, for example, methylmercapto, ethylmercapto, propylmercapto, isopropylmercapto, butylmercapto, isobutylmercapto, tert.-butylmercapto, pentylmercapto, hexylmercapto or heptylmercapto.

Lower alkanoyl is a straight-chain or branched lower alkylcarbonyl group with 1 to 8, preferably up to 5, carbon atoms, and denotes, for example, formyl, acetyl, propionyl butyryl, valeryl, isovaleryl or heptanecarbonyl.

Halogen is fluorine, chlorine or bromine.

Aryl is a monocyclic or polycyclic, such as bicyclic or tricyclic, aromatic radical with up to 14 carbon atoms and is, for example, phenyl, naphthyl or anthranyl, which can optionally be substituted, for example by hydroxyl, lower alkoxy, lower alkyl, halogen or nitro. Aroyl is a corresponding arylcarbonyl radical, for example benzoyl.

Examples of substituents of the phenyl group $R_1$ are optionally protected hydroxyl, lower alkyl, such as methyl, lower alkoxy, such as methoxy, halogen atoms, such as fluorine or chlorine, halogeno-lower alkyl, such as trifluoromethyl, optionally protected amino, nitro, optionally protected amino-lower alkyl, such as aminomethyl, carbamoyl, carbamoyloxy or carbamoylamino, which are optionally N-monosubstituted or N,N-disubstituted, for example by lower alkyl, such as methyl, or acyl, especially lower alkanoyl, such as acetyl, the substituents being in the o-, m- or preferably the p-position.

The substituent $R_2$ is, in particular, a free carboxyl group or an esterified carboxyl group which can be split physiologically, for example an esterified carboxyl group which can be split enzymatically.

Esterified carboxyl groups which can be split physiologically are, above all, those which can be split enzymatically or be split by the acid gastric juice. These esters are readily resorbable in the organism and can therefore be used therapeutically as such. Esters of this type are described, for example, in British patent specification No. 1,229,453, in Belgian Pat. No. 789,821 and in German Patent Applications Nos. DT 1,951,012, DT 2,228,012 and DT 2,230,620. Such esters are derived, for example, from indan-1-ol or 5-hydroxyindan-1-ol or 3,4-benzo-5-oxo-tetrahydro-2-furanol or from alcohols of the formula HO—$CH_2OCO$—$R_2'$, wherein $R_2'$ can represent an alkyl radical or aminoalkyl radical or a cycloalkyl radical with 3-7 carbon atoms. In particular, $R_2'$ denotes a lower alkyl radical, such a methyl, ethyl, isopropyl and above all tert.-butyl, an α-amino-lower alkyl radical, such as 1-amino-2-methylpropyl or 1-amino-3-methylbutyl, or a cyclopentyl or cyclohexyl radical.

A lower alkoxy group $R_3$ contains 1 to 7, preferably 1 to 4, carbon atoms and is in particular methoxy (compare Netherlands Application No. 73/09,136). Substituents of the methyl group $R_3$ are, above all, free, esterified or etherified hydroxyl or mercapto groups, and also optionally N-substituted carbamoyloxy or thiocarbamoylmercapto groups, or quaternary ammonium groups.

An esterified hydroxyl or mercapto group in a substituted methyl group $R_3$ contains, as the acid radical, above all the radical of a carboxylic acid or thiocarboxylic acid, for example lower alkanoyl, which is optionally substituted by halogen atoms, especially chlorine, such as formyl, propionyl, butyryl, pivaloyl or chloroacetyl, but especially acetyl, or aroyl or aryl-lower alkanoyl optionally substituted by, for example, lower alkyl, lower alkoxy, halogen or nitro, for example benzoyl or phenylacetyl, and also, as a thiocarboxylic acid radical, in particular thioaroyl which is optionally substituted as mentioned, and above all thiobenzoyl. Esterified mercapto groups can in particular also contain heteroyl, wherein the heterocyclyl radical preferably contains 5–6 ring members and, as hetero-atoms, nitrogen, optionally in the N-oxidised form, and/or oxygen or sulphur, for example optionally 1-oxidised pyridyl, pyrimidyl, pyridazinyl, thiadiazolyl, oxadiazolyl or N-methyltetrazolyl. in addition, hydroxyl groups esterified by hydrogen halide acids should be mentioned; the methyl group $R_3$ can therefore be substituted by, or example, fluorine, chlorine or bromine.

Etherified hydroxyl groups in a substituted methyl group $R_3$ are described, for example, in Belgian Pat. No. 719,710. Lower alkoxy, such as methoxy, ethoxy or n-propoxy, should be singled out.

Etherified mercapto groups in a substituted methyl group $R_3$ for example contain, as the etherifying radicals, lower alkyl, for example methyl, and also optionally substituted phenyl or heterocyclyl. Phenyl can be substituted by, for example, lower alkyl, lower alkoxy, halogen or nitro. The heterocyclyl radicals contain, as hetero-atoms, nitrogen, optionally in the N-oxidised form, and/or oxygen or sulphur. Examples to be mentioned are optionally 1-oxidised pyridyl, pyrimidyl, pyridazinyl, pyrazinyl, imidazolyl, imidazolidyl, purinyl, triazolyl and tetrazolyl. These radicals can be substituted, for example, by lower alkyl, lower alkoxy, hydroxyl or halogen. Optionally substituted heterocyclyl radicals of aromatic character, with 5 ring atoms which comprise 2 nitrogen atoms and a further oxygen or sulphur atom or 1 to 2 further nitrogen atoms, should be singled out particularly. Preferred substituents are lower alkyl radicals with 1-5 carbon atoms such as methyl, ethyl, propyl, isoproyl, n-butyl, isobutyl and tert.butyl, lower alkoxy or lower alkylthio radicals with 1-5 carbon atoms, particularly methylthio, cycloalkyl radicals with 13-7 carbon atoms, for example cyclopentyl or cyclohexyl, or aryl radicals, such as phenyl or substituted phenyl, for example phenyl substituted by one or more nitro groups or halogen atoms or lower alkyl or lower alkoxy groups, or unsubstituted or substituted thienyl, particularly 2-thienyl, or thienyl substituted as indicated for phenyl, or, in particular, optionally monosubstituted or disubstituted amino groups, for example amino, lower alkylamino, which optionally contains carboxyl or amino, such as methylamino, 2-carboxyethylamino or 2-aminoethylamino, acylamino, such as lower alkanoylamino, which optionally contains carboxyl or amino, such as acetylamino or especially β-carboxypropionylamino or α-aminoacetylamino, or lower alkoxycarbonylamino, such as tert.-butoxycarbonylamino or tert.amyloxycarbonylamino, or sulphonylamino.

The following should be mentioned as examples of the heterocyclyl radical which etherifies the mercapto group:

Triazolyl optionally substituted by lower alkyl and/or aryl, such as phenyl, such as 1H-1,2,3-triazol-5-yl, 1-methyl-1H-1,2,3-triazol-4-yl, 1H-1,2,4-triazol-3-yl, 5-methyl-1H-1,2,4-triazol-3-yl, 3-methyl-1-phenyl-1H-1,2,4-triazol-5-yl, 4,5-dimethyl-4H-1,2,4-triazol-3-yl and 4-phenyl-4H-1,2,4-triazol-3-yl, tetrazolyl optionally substituted by lower alkyl or aryl, such as phenyl or chlorophenyl, such as 1H-tetrazol-5-yl, 1-methyl-1H-tetrazol-5-yl, 1-ethyl-1H-tetrazol-5-yl, 1-n-propyl-1H-tetrazol-5-yl, 1-phenyl-1H-tetrazol-5-yl and 1-p-chlorophenyl-1H-tetrazol-5-yl, thiazolyl optionally substituted by, for example, lower alkyl or heterocyclyl, such as thienyl, such as 2-thiazolyl, 4-(2-thienyl)-2-thiazolyl and 4,5-dimethyl-2-thiazolyl, thiadiazolyl optionally substituted by lower alkyl, amino, lower alkylamino which optionally contains carboxyl or amino, such as methylamino, 2-carboxyethylamino or 2-aminoethylamino, or lower alkanoylamino which optionally contains carboxyl or amino, such as, in particular, β-carboxypropionylamino or α-aminoacetylamino, such as 1,3,4-thiadiazol-2-yl, 2-methyl-1,3,4-thiadiazol-5-yl, 2-ethyl-1,3,4-thiadiazol-5-yl, 2-n-propyl-1,3,4-thiadiazol-5-yl, 2-isopropyl-1,3,4-thiadiazol-5-yl, 2-amino-1,3,4-thiadiazol-5-yl and 2-(β-carboxypropionylamino)-1,3,4-thiadiazol-5-yl, 5-thiatriazolyl, oxazolyl, isoxazolyl or oxadiazolyl optionally substituted by, for example, lower alkyl and/or aryl, such as 5-oxazolyl, 4-methyl-5-oxazolyl, 2-oxazolyl, 4,5-diphenyl-2-oxazolyl, 3-methyl-5-isoxazolyl, 1,2,4-oxadiazol-5-yl, 2-methyl-1,3,4-oxadiazol-5-yl, 2-phenyl-1,3,4-oxadiazol-5-yl, 5-β-nitrophenyl-1,3,4-oxadiazol-2-yl and 2-(2-thienyl)-1,3,4-oxadiazol-5-yl, as well as bicyclic heterocyclyl radicals which are optionally substituted by halogen or nitro, such as 2-benzimidazolyl, 5-chloro-2-benzimidazolyl, 2-benzoxazolyl, 5-nitro-2-benzoxazolyl, 5-chloro-2-benzoxazolyl, s-triazolo[4.3-a]pyrid-3-yl, 3H-v-triazolyl[4.5-b]pyrid-5-yl, purin-2-yl, purin-6-yl and 8-chloro-2-methylpyrin-6-yl.

An optionally N-substituted carbamoyloxy group or thiocarbamoylmercapto group in a substituted methyl group $R_3$ is, for example, a group of the formula —O—CO—NH—$R^{II}$ (French Pat. No. 1,463,831), wherein $R^{II}$ is hydrogen or an optionally halogen-substituted lower alkyl radical, or a group of the formula —S—C(=S)—N($R^{II}$)($R^{III}$), wherein $R^{II}$ has the abovementioned meaning and $R^{III}$ represents hydrogen or has the abovementioned meaning of $R^{II}$ [compare J. Med. Chem. 8, 174 (1965)]. Above all, $R^{II}$ is methyl, ethyl or chlorine-substituted methyl or ethyl, especially β-chloroethyl.

In a quaternary ammonium-methyl group $R_3$, the ammonium part is preferably an unsubstituted or substituted pyridinium group. Examples of substituents of the pyridinium group which should be mentioned are those listed in Antimicrobial Agents and Chemotherapy 1966, page 573-580, such as unsubstituted or substituted, for example hydroxyl-substituted or carboxyl-substituted, lower alkyl, for example methyl, ethyl, propyl, hydroxymethyl or carboxymethyl, halogen, such as fluorine, chlorine, bromine or iodine, or trifluoromethyl, hydroxyl, sulpho, carboxyl, cyano, lower alkoxycarbonyl, such as methoxycarbonyl or ethoxycarbonyl, lower alkylcarbonyl, such as methylcarbonyl, and, in particular, carbamoyl which is unsubstituted or substituted, for example carbamoyl substituted by lower alkyl, hydroxy-lower alkyl or halogeno-lower alkyl, especially chloro-lower alkyl, such as N-methylcarbamoyl, N-isopropylcarbamoyl and N-β-chloroethylcarbamoyl, but above all carbamoyl. The substituents can be in the 2-, 3- and/or 4-position, but are preferably in the 3- or 4-position.

The radical B can be monocyclic, bicyclic or tricyclic and in particular comprises optionally polysubstituted and/or optionally partially hydrogenated pyridine, pyrazine, pyridazine, triazine, quinoline, isoquinoline, naphthyridine or pyrido-pyrimidine radicals which are optionally substituted at the nitrogen-containing ring by 1 or 2 optionally, in particular physiologically splittably, esterified, or etherified hydroxyl or mercapto groups or optionally mono- or di-lower alkylated or lower alkanoylated amino groups or by halogen, and the tautomers of these radicals.

Radicals B to be singled out for example have the formula ($B_1$)

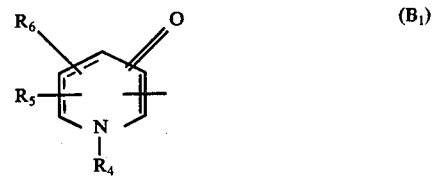

wherein $R_4$ denotes lower alkyl, especially methyl, and $R_5$ and $R_6$ substitute adjacent ring carbon atoms and conjointly represent a lower alkylene radical, which optionally carries an oxo group, especially a 1,3-propylene, 1,4-butylene or 1,5-pentylene radical, or represent a radical of the formula

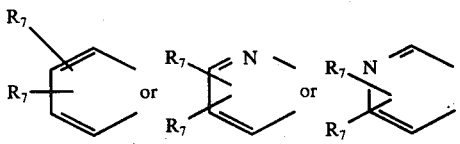

wherein the two $R_7$ independently of one another denote hydrogen, hydroxyl, lower alkyl, especially methyl, lower alkoxy, especially methoxy, lower alkylmercapto, especially methylmercapto, lower alkanoyl, especially acetyl, lower alkanoylamino, especially acetylamino, lower alkoxycarbonyloxy, especially ethoxycarbonyloxy, lower alkylsulphonyl, especially methylsulphonyl or aryl, especially phenyl, or the two $R_7$ conjointly with the group —CH=CH— form a thiazole, isothiazole, pyrrole, furane or benzene ring which, for example, can be substituted by an oxo group, a lower alkyl group, such as a methyl group, or a lower alkonoyl group, such as an acetyl group, and wherein the broken line denotes a 4,5- or 5,6-double bond, or have the formula ($B_2$)

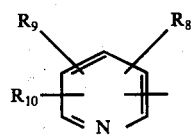

wherein $R_8$ denotes a free hydroxyl or mercapto group, an etherified hydroxyl or mercapto group, such as a lower alkylated, for example methylated, hydroxyl or mercapto group, or an esterified hydroxyl or mercapto group, especially a physiologically splittable esterified hydroxyl or mercapto group, such as a hydroxyl or mercapto group esterified with a half-ester of carbonic acid, for example monoethyl carbonate, a free amino group or a mono- or di-lower alkylated, such as methylated, amino group, or a lower alkanoylated, such as acetylated, or a carbamoylated amino group or halogen, especially chlorine, $R_9$ represents hydrogen or has the meaning of $R_8$ or represents nitrile, lower alkyl, such as methyl, hydroxy-lower alkyl, such as 1-hydroxyethyl, lower alkanoyl, such as acetyl, aryl, especially phenyl, or arylcarbonyl, especially phenylcarbonyl, $R_{10}$ represents hydrogen, nitrile, lower alkyl, especially methyl, lower alkanoyl, especially acetyl, or aryl, especially phenyl, or $R_9$ and $R_{10}$ conjointly represent a lower alkylene radical, which optionally carries an oxo group, especially a 1,3-propylene, 1,4-butylene or 1,5-pentylene radical, or $R_9$ and $R_{10}$ substitute adjacent ring carbon atoms and conjointly represent a radical of the formula

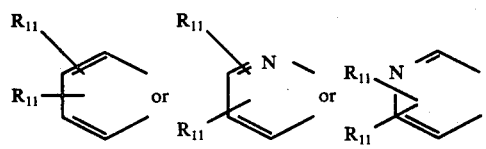

wherein the two $R_{11}$ independently of one another denote hydrogen, hydroxyl, optionally halogenated lower alkyl, such as methyl or trifluoromethyl, lower alkoxy, such as ethoxy, lower alkanoyloxy, such as acetoxy, mercapto, lower alkylmercapto, especially methylmercapto, lower alkanoyl, especially acetyl, amino, mono- or di-lower alkylamino, such as dimethylamino, lower alkanoylamino, such as acetylamino, lower alkyloxycarbonylamino optionally substituted by phenyl, such as ethoxycarbonylamino or benzyloxycarbonylamino, lower alkylsulphonyl, especially methylsulphonyl, or aryl, especially phenyl, or the two $R_{11}$ conjointly with the group —CH=CH— form a thiazole, isothiazole, pyrrole, furane or benzene ring, which can be substituted by an oxo group, a lower alkyl group, such as a methyl group, or a lower alkanoyl group, such as an acetyl group, or the two $R_{11}$ in adjacent positions conjointly denote the methylenedioxy group or a lower alkylene radical, especially the 1,3-propylene, 1,4-butylene or 1,5-pentylene radical, or $R_9$ and $R_{10}$ conjointly represent a group of the formula

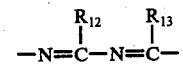

wherein $R_{12}$ denotes hydrogen, hydroxyl or lower alkyl, especially methyl, lower alkoxy, especially methoxy, amino, mono- or di-lower alkylamino, especially dimethylamino, or lower alkoxycarbonylamino optionally substituted by phenyl, such as ethoxycarbonylamino or benzyloxycarbonylamino, and $R_{13}$ denotes hydrogen, lower alkyl, especially methyl, or lower alkoxy, especially methoxy, or have the formula ($B_3$)

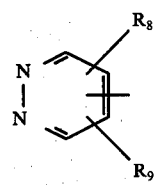

wherein $R_8$ and $R_9$ have the meaning mentioned under formula ($B_2$), or have the formula ($B_4$)

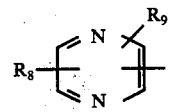

wherein $R_8$ and $R_9$ have the meaning mentioned under formula ($B_2$), or have the formula ($B_5$)

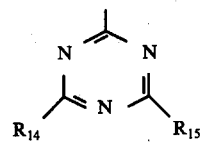

wherein $R_{14}$ and $R_{15}$ independently of one another denote hydrogen, halogen, especially chlorine, a free hydroxyl or mercapto group, an etherified hydroxyl or mercapto group, especially a lower alkylated, such as methylated, hydroxyl or mercapto group, or an esterified hydroxyl or mercapto group, especially a physiologically splittable esterified hydroxyl or mercapto group, such as a hydroxyl or mercapto group esterified with a half-ester of carbonic acid, for example monoethyl carbonate, or an optionally mono- or di-lower alkylated, especially dimethylated, amino group or a lower alkanoylated, such as acetylated, or a carbamoylated amino group, or have the formula (B₆)

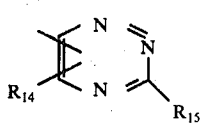

wherein R₁₄ and R₁₅ have the meaning mentioned under formula (B₅), the substituent R₁₄ preferably occupying the 5-position of the as-triazine ring, or, where appropriate, have a formula tautomeric thereto.

Compounds to be singled out are those of the formula I, wherein R₁ has the meaning mentioned under formula I and phenyl is in particular substituted by hydroxyl, such as p-hydroxyl, R₂ denotes a carboxyl group, R₃ denotes hydrogen, lower alkoxy, lower alkanoyloxymethyl, lower alkoxymethyl, aroylthiomethyl, optionally substituted pyridiniomethyl, or heterocyclylmercaptomethyl, the heterocyclyl radical having 5 ring atoms and being of aromatic character, being optionally substituted and containing, in addition to 2 nitrogen atoms, at least one further ring hetero-atom from the group nitrogen, oxygen or sulphur, especially optionally substituted thiadiazolylmercaptomethyl, such as thiadiazolylmercaptomethyl substituted by amino or 3-carboxypropionylamino, triazolylmercaptomethyl, or tetrazolylmercapto methyl optionally substituted by lower alkyl, such as methyl, and B denotes one of the groups B₁ to B₆, especially a group B₂, B₃ or B₆ which is mono- to di-substituted exclusively by hydroxyl, halogen, such as chlorine, mercapto and/or methylmercapto, and salts thereof.

The invention relates above all to compounds of the formula I, wherein R₁ has the meaning mentioned under formula I and in particular represents phenyl, R₂ denotes a carboxyl group, R₃ denotes hydrogen, lower alkoxy, such as methoxy, lower alkanoyloxymethyl, such as acetoxymethyl, aroylthiomethyl, such as benzoylthiomethyl, optionally substituted pyridiniomethyl, such as 4-carbamoylpyridiniomethyl, or heterocyclylmercaptomethyl, the heterocyclyl radical having 5 ring atoms and being of aromatic character, being optionally substituted and containing, in addition to 2 nitrogen atoms, at least one further ring hetero atom from the group nitrogen, oxygen or sulphur, especially optionally substituted thiadiazolylmercaptomethyl, such as thiadiazolylmercaptomethyl substituted by amino or 3-carboxypropionylamino, triazolylmercaptomethyl, or tetrazolylmercaptomethyl which is optionally substituted by lower alkyl, such as methyl, such as 2-amino-1,3,4-thiadiazol-5-yl-mercaptomethyl, 2-(3-carboxypropionylamino)-1,3,4-thiadiazol-5-ylmercaptomethyl, 1,2,3-1H-triazol-5-ylmercaptomethyl or 1-methyl-1H-tetrazol-5-ylmercaptomethyl, and the group B denotes pyridine which is mono- to di-substituted by hydroxyl or chlorine, quinoline substituted by hydroxyl, pyridazine substituted by hydroxyl, or 1,3,4-triazine di-substituted by hydroxyl and/or methylmercapto, or a tautomer thereof, and to salts thereof.

Compounds to be singled out in particular are those of the formula I, wherein R₁ has the meaning mentioned under formula I and in particular represents phenyl, R₂ denotes a carboxyl group, R₃ denotes lower alkoxy, such as methoxy, lower alkanoyloxymethyl, such as acetoxymethyl, aroylthiomethyl, such as benzoylthiomethyl, optionally substituted pyridiniomethyl, such as 4-carbamoyl-pyridiniomethyl, or heterocyclylmercaptomethyl, the heterocyclyl radical having 5 ring atoms and being of aromatic character, being optionally substituted and containing, in addition to 2 nitrogen atoms, at least one further ring hetero-atom from the group nitrogen, oxygen or sulphur, especially optionally substituted thiadiazolylmercaptomethyl, triazolylmercaptomethyl, or tetrazolymercaptomethyl, optionally substituted by lower alkyl, such as methyl, such as 2-amino-1,3,4-thiadiazol-5-ylmercaptomethyl, 2-(3-carboxypropionylamino)-1,3,4-thiadiazol-5-ylmercaptomethyl, 1,2,3-1H-triazol-5-ylmercaptomethyl or 1-methyl-1H-tetrazol-5-ylthiomethyl, and the group B denotes 2-hydroxypyrid-5-yl, 6-hydroxypyridazin-3-yl, 2-hydroxyquinolin-4-yl, 2,6-dichloropyrid-4-yl, 3,5-dihydroxy-1,2,4-triazin-6-yl or 3-methylthio-6-hydroxy-1,2,4-triazin-6-yl, or a tautomer thereof, and their salts.

Salts of compounds of the present invention are, above all, pharmaceutically usable non-toxic salts of those compounds which are able to form salts with bases. Such salts are, above all, metal salts or ammonium salts, such as alkali metal salts or alkaline earth metal salts, for example sodium, potassium, magnesium, calcium or aluminium salts, as well as ammonium salts with ammonia or suitable organic amines, the amines used for forming the salt being, above all, aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tris-(2-hydroxyethyl)-amine, basic aminoacids such as lysine, ornithine and argenine, basic aliphatic esters of carboxylic acids, for example 4-aminobenzoic acid 2-diethylaminoethyl ester, lower alkyleneamines, for example 1-ethylpiperidine, cycloalkylamines, for example bicyclohexylamine, or benzylamines, for example N,N'-dibenzylethylenediamine, and also bases of the pyridine type, for example pyridine, collidine or quinoline.

Further salts are derived from the compounds according to the invention which have a basic group, for example an unsubstituted or monoalkylated or dialkylated amino group. Such compounds either form inner salts with the free carboxyl group R₂ or can be converted into a salt with a pharmaceutically usable, non-toxic organic or inorganic acid. Suitable acids are organic carboxylic acids or sulphonic acids, for example alkanoic acids, such as trifluoroacetic acid or methanesulphonic acid, or aromatic acids, such as benzoic acid or benzenesulphonic acid, or inorganic acids, such as hydrochloric acid, sulphuric acid or phosphoric acid.

The new compounds can be in the form of mixtures of isomers, for example racemates, or in the form of individual isomers, for example optically active antipodes.

The new compounds of the formula I exhibit a pharmacological action, in particular an especially pronounced antibacterial action. Thus they are active against Gram-positive bacteria, such as staphylococci, or against Gram-negative bacteria, such as enterobacteriaceae, for example strains of Escherichia, and especially against strains of Pseudomonas.

For example, they inhibit the growth of enterobacteriaceae and staphylococci and pseudomonads in vitro in concentrations of about 0.15 to 60 µg/ml. In mice, they are active, on subcutaneous administration, against staphylococci, such as Staphylococcus aureus, in a dosage range of about 8 to about 100 mg/kg, against enterobacteriaceae, such as *Escherichia coli,* in a dosage range from about 250 to about 280 mg/kg, and against pseudomonads, such as *Pseudomonas aeruginosa,* in a dosage range of about 50 to about 200 mg/kg. The compounds of the formula I or their pharmaceutically acceptable salts, for example 7β-[D(−)-α-(3,5-dioxo-2,3,4,5-tetrahydro-1,2,4-triazine-6-carboxamido)-phenylacetamido]-cephalosporanic acid, can therefore be used to combat infections which are caused by such microorganisms, and also as feedingstuff additives, for the preservation of foodstuffs or as disinfectants.

The compounds of the present invention are manufactured according to methods which are in themselves known. For example, they can be manufactured by a. acylating the primary amino group in a compound of the formula II

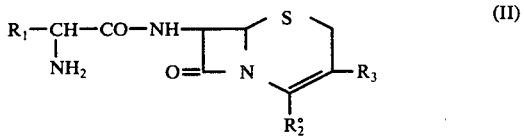

wherein $R_1$ has the indicated meaning, $R_2^o$ has the meaning of $R_2$ or represents an easily splittable esterified carboxyl group and $R_3$ has the indicated meaning, or in a salt thereof, by treatment with an acid of the formula B—COOH (III), wherein B has the indicated meaning, or with a reactive functional derivative thereof, or by b. acylating a compound of the formula IV

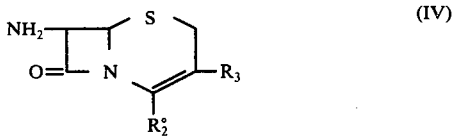

wherein $R_2^o$ has the meaning of $R_2$ or represents an easily splittable esterified carboxyl group and $R_3$ has the indicated meaning, or a salt thereof, with a carboxylic acid of the formula (V)

wherein $R_1$ and B have the indicated meanings, or with a reactive functional derivative thereof, and, if appropriate, in a resulting compound, splitting off a protective group present in the radical B and/or converting an easily splittable esterified carboxyl group $R_2^o$ into a free carboxyl group $R_2$ or a physiologically splittable esterified carboxyl group $R_2$ and/or, if desired, converting an optionally substituted methyl group $R_3$ into another group $R_3$ and/or, if desired, converting a compound obtained as the free acid into a salt, or a salt obtained into the free acid, and/or separating an isomer mixture obtained into the individual isomers.

An easily splittable esterified carboxyl group $R_2^o$ in a starting material of the formula II or IV is, in particular, an ester group which can be split to the free carboxyl group in a neutral, acid or weakly alkaline medium, solvolytically, for example hydrolytically, alcoholytically or acidolytically, or reductively, for example hydrogenolytically.

Esterified carboxyl groups $R_2^o$ which can easily be split by solvolysis with a solvent containing hydroxyl groups, for example water or alcohols, such as, for example, methanol or ethanol, preferably under neutral conditions, are above all those which are derived from silyl alcohol or stannyl alcohol. Such groups are described, for example, in British patent specifications Nos. 1,073,530 and 1,211,694 and in German Offenlegungsschrift No. 1,800,698. Examples which may be mentioned are tri-lower alkyl-silyloxycarbonyl, such as trimethyl-silyloxycarbonyl and tert.-butyl-dimethyl-silyloxycarbonyl, lower alkoxy-lower alkyl-halogeno-silyloxycarbonyl, for example chloro-methoxy-methyl-silyloxycarbonyl, or trilower alkyl-stannyloxycarbonyl, for example tri-n-butylstannyloxycarbonyl.

Esterified carboxyl groups $R_2^o$ which are split easily by acidolysis, for example in the presence of hydrogen chloride, hydrogen fluoride or hydrogen bromide or of organic acids, such as acetic acid, trifluoroacetic acid or formic acid, if appropriate with the addition of a nucleophilic compound, such as phenol or anisole, are derived from lower alkanols which are poly-branched in the α-position or lower alkanols which contain one or more electron donors in the α-position. Examples of such esterified carboxyl groups are tert.butoxycarbonyl, tert.amyloxycarbonyl, cyclopentyloxycarbonyl, cyclohexyloxycarbonyl, adamantyloxycarbonyl, furfuryloxycarbonyl, p-methoxy-benzyloxycarbonyl, diphenylmethoxycarbonyl and pivaloyloxymethoxycarbonyl. Esterified carboxyl groups $R_2^o$ which can be split by reduction, for example with zinc and acid, are above all derived from 2-halogeno-lower alkanols, for example from 2,2,2-trichloroethanol and 2-iodoethanol. Carboxyl groups $R_2^o$ esterified by phenacyl alcohol or p-nitrobenzyl alcohol can be split by hydrogenolysis, for example by treatment with nascent hydrogen or with hydrogen in the presence of a noble metal catalyst, for example a palladium catalyst.

Salts of starting materials of the formula II or IV are, in particular, salts of those compounds which have a free carboxyl group, above all ammonium salts, such as trilower alkylammonium salts, for example triethylammonium salts, and also alkali metal salts.

The acylation of the amino group of the compound II with the carboxylic acid of the formula III is carried out in accordance with methods which are in themselves known, in particular in the manner known from penicillin chemistry and cephalosporin chemistry for the acylation of weakly basic amino groups. The acylating agent used is either the corresponding acid of the formula III, in which case the reaction is carried out in the presence of a condensation agent, for example a carbodiimide, such as N,N'-diethyl-, N,N'-dipropyl-, N,N'-diisopropyl-, N,N'-dicyclohexyl- or N-ethyl-N'-γ-dimethylamino-propylcarbodiimide, or in the presence of a suitable carbonyl compound, for example N,N'-carbonyldiimidazole, or of isoxazolium salts, for example N-ethyl-5-phenyl-isoxazolinium-3'-sulphonate or N-tert.butyl-5-methyl-isoxazolinium perchlorate, or of an acylamino compound, for example 2-ethoxy-1-ethoxycarbonyl-1,2-dihydroquinoline, or is a reactive functional derivative, above all an acid halide, especially an acid chloride or acid bromide, or, for example, an activated ester, for example a p-nitrophenyl ester, 2,4-dinitrophenyl ester, 2,4,5- or 2,4,6-trichlorophenyl ester or pentachlorophenyl ester or, for example, the cyanomethyl ester, N-hydroxysuccinimide ester, N-hydroxypiperidine ester or N-hydroxyphthalimide ester, or a mixed anhydride, for example a mixed anhydride with mono-esterified carbonic acid, such as a carbonic acid lower alkyl ester, for example the ethyl ester or methyl ester, or a mixed anhydride with an optionally halogen-substituted lower alkanoic acid such as formic acid, pivalic acid or trichloroacetic acid. If a hydroxyl group is present in the α-position relative to the carboxyl group in the group B, a mixed inner anhydride having the partial formula

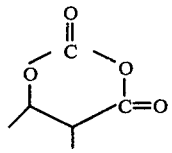
(IIIa)

can also be used for the acylation.

The acylation reaction is carried out in a solvent or diluent, if desired in the presence of a catalyst and/or in the presence of basic agents such as aliphatic, aromatic or heterocyclic nitrogen bases, for example triethylamine, diisopropylethylamine, N,N-diethylaminoacetic acid ethyl ester, N-methylmorpholine, N,N-dimethylaniline, pyridine, 2-hydroxypyridine, p-dimethylaminopyridine, collidine or 2,6-lutidine.

The solvents or diluents used are inert liquids, for example carboxylic acid amides, such as N,N-di-lower alkylamides, for example dimethylformamide or hexamethylphosphoric acid triamide, halogenated hydrocarbons, for example methylene chloride, carbon tetrachloride or chlorobenzene, ketones, for example acetone, esters, for example ethyl acetate, nitriles, for example acetonitrile, solvents containing oxa groups, such as tetrahydrofurane and dioxane, or mixtures thereof.

The reaction is carried out at room temperature or with cooling or warming, for example at temperatures of −70° to +100° C, if appropriate in an inert gas atmosphere, for example a nitrogen atmosphere, and/or with exclusion of moisture.

In carrying out the acylation, free hydroxyl, mercapto, amino and/or carboxyl groups which may be present in the reactants are advantageously protected, especially by protective groups which can be split off easily, such as are known, for example, from the synthesis of peptides, compare Schröder and Lübke "The Peptides", vol. 1, Academic Press, New York and London, 1965, and Th. Wieland, Angew. Chem. 63 (1951), 7–14, 66 (1954), 507–512, 69 (1957), 362–372, 71 (1959), 417–425 and 75 (1963), 539–551. Examples of amino protective groups which may be mentioned are optionally substituted aralkyl groups, such as diphenylmethyl or triphenylmethyl groups, or acyl groups, such as formyl, trifluoroacetyl, phthaloyl, p-toluenesulphonyl, benzylsulphonyl, benzenesulphenyl or o-nitrophenylsulphenyl, or, above all, groups derived from carbonic acid or thiocarbonic acid, such as carbobenzoxy groups optionally substituted in the aromatic radical by halogen atoms, nitro groups or lower alkyl or lower alkoxy or lower carbalkoxy groups, for example carbobenzoxy, p-bromocarbobenzoxy or p-chlorocarbobenzoxy, p-nitrocarbobenzoxy or p-methoxycarbobenzoxy, coloured benzyloxycarbonyl groups, such as p-phenylazobenzyloxycarbonyl and p-(p'-methoxyphenylazo)-benzyloxycarbonyl, tolyloxycarbonyl, 2-phenyl-isopropoxycarbonyl, 2-tolyl-isopropoxycarbonyl and, above all, 2-(para-biphenylyl)-2-propoxycarbonyl, and also aliphatic oxycarbonyl groups, such as, for example, allyloxycarbonyl, cyclopentyloxycarbonyl, tert.amyloxycarbonyl, adamantyloxycarbonyl, 2,2,2-trichloroethoxycarbonyl, 2-iodoethoxycarbonyl and, above all, tert.butoxycarbonyl, and, for example, carbamoyl, thiocarbamoyl, N-phenylcarbamoyl and N-phenylthiocarbamoyl. Easily splittable ester groups which can be prepared to protect a free carboxyl group have already been indicated above. Hydroxyl groups or mercapto groups can be protected by etherification, for example with tert. butanol, or in the form of a trityl ether, a silyl ether, or a stannyl ether, or by esterification, for example with a half-ester of a carbonic acid half-halide, such as ethoxycarbonyl chloride.

The acylation of the amino group of the compound IV with the carboxlic acid of the formula V is carried out analogously.

In a compound obtained according to the invention, hydroxyl, mercapto, amino and carboxyl protective groups can be split off in a manner which is in itself known by solvolysis, for example hydrolysis, alcoholysis or acidolysis, or by reduction, for example by hydrogenolysis.

In resulting compounds of the formula I, a substituted methyl group can be converted into another group of this type. Thus, for example, a compound containing an esterified hydroxymethyl radical $R_3$, wherein the esterified hydroxyl group in particular denotes lower alkanoyloxy, for example acetoxy, can first be reacted with thiobenzoic acid and then be treated with pyridine in the presence of a mercury salt, or can be reacted with a suitable salt, such as potassium thiocyanate, potassium iodide or potassium nitrate, and with pyridine in the presence of water at a pH value of about 6.5, obtained, for example, by means of phosphoric acid, thus giving the corresponding pyridiniummethyl compound which can, if required, be converted to the inner salt (the zwitter ion form), for example by treatment with a suitable ion exchange reagent. The pyridinium compound can also be manufactured in accordance with the process of Belgian Pat. No. 719,711 (DOS 1,795,643) by first converting the acetoxy group into a group more suitable for nucleophilic exchange, for example a halogen atom or an acetoxy group which contains an electron-attracting substituent, such as, for example, chloroacetoxy, dichloroacetoxy or cyanoacetoxy. Furthermore, compounds containing a lower alkanoyloxymethyl group, for example an acetoxymethyl group, as the radical $R_3$ can be reacted with a mercapto compound, such as an optionally substituted lower alkylmercaptan, phenylmercaptan or heterocyclylmercaptan, thus giving compounds of the formula I, wherein $R_3$ represents an etherified mercaptomethyl group. The reaction is carried out in water or in a mixture of water and a water-miscible solvent, such as acetone, dioxane, dimethylformamide, tetrahydrofurane, hexamethylphosphoric acid triamide and the like, in the presence of a base, such as an alkali metal bicarbonate, for example sodium bicarbonate, at a pH value of about 7 to 7.8, at temperatures from about 10° to about 100° C, preferably at about 50° to about 60° C, and in an inert gas atmosphere, such as a nitrogen atmosphere.

Salts of compounds of the formula I can be manufactured in a manner which is in itself known. Thus, salts of compounds of the formula I, wherein $R_2$ represents a free carboxyl group, can be formed, for example, by treatment with metal compounds, such as alkali metal salts of suitable carboxylic acids, for example with the sodium salt of α-ethylcaproic acid, or with ammonia or a suitable organic amine.

Salts can be converted into the free compounds in the usual manner, metal salts and ammonium salts, for example, by treatment with suitable acids or ion exchangers.

Resulting mixtures of isomers can be separated into the individual isomers according to methods which are in themselves known, for example by fractional crystallisation, adsorption chromatography (column chromatography or thin layer chromatography) or other suitable methods of separation. Resulting racemates can be separated into the antipodes in the usual manner, if appropriate after the introduction of suitable salt-forming groupings, for example by forming a mixture of diastereoisomeric salts with optically active salt-forming agents, separating the mixture into the diastereoisomeric salts and converting the separated salts into the free compounds, or by fractional crystallisation from optically active solvents.

The process also embraces those embodiments according to which compounds obtained as intermediates are used as starting materials and the remaining process steps are carried out with these, or the process is discontinued at any stage; furthermore, starting materials can be used in the form of derivatives or be formed during the reaction.

Preferably, those starting materials are used, and the reaction conditions are so chosen, that the compounds mentioned initially as being particularly preferred are obtained.

The starting materials of the formula II, III and IV are known or can be manufactured according to known processes.

Compounds of the formula V and their reactive functional derivatives have not previously been disclosed. They can be obtained in a manner which is in itself known, by acylating a compound of the formula $R_1$—CH(NH$_2$)—COOH (VI), in which the carboxyl group is present in a protected form, for example in the form of an easily splittable esterified carboxyl group, with a carboxylic acid of the formula B—COOH (III), with a halide thereof or with a mixed anhydride thereof, then splitting off the carboxyl protective group and, if desired, converting the carboxylic acid obtained into a reactive functional derivative thereof.

Easily splittable esters of carboxylic acids of the formula VI are, in particular, those which after acylation of the amino group can be split solvolytically, for example hydrolytically, alcoholytically or especially acidolytically, or reductively, to give the free carboxylic acid of the formula V. Such easily splittable ester groups are derived from the same alcohols from which the easily splittable esterified carboxyl groups $R_2^o$ are derived, and the subsequent splitting is carried out analogously. Benzyl esters of compounds of the formula VI which, after N-acylation, can be split reductively, for example by means of palladium and hydrogen, are preferred.

The acylation of the amino group in a compound of the formula (VI), in which the carboxyl group is protected, is carried out analogously to the acylation of the amino group in a compound of the formula (II), it being possible to use the same halides, mixed anhydrides or inner mixed anhydrides having the partial formula (IIIa), of the carboxylic acid of the formula III, or this carboxylic acid itself.

The conversion of a resulting carboxylic acid of the formula (V) into a reactive functional derivative thereof is carried out in a manner which is in itself known.

Carboxylic acid chlorides are obtained, for example, by treatment with thionyl chloride, activated esters are obtained, for example, by reaction of this resulting carboxylic acid chloride with an appropriate hydroxy compound, for example p-nitrophenol or N-hydroxyphthalimide, and mixed anhydrides are obtained by reaction of a carboxylic acid of the formula (V) with an appropriate halide, for example chloride, of a second carboxylic acid, for example a mono-esterified carbonic acid, such as a carbonic acid lower alkyl ester, for example the ethyl ester or methyl ester, or an optionally halogen-substituted lower alkanoic acid, such as formic acid, pivalic acid or trichloroacetic acid. When forming the mixed anhydride, a simultaneously present hydroxyl or mercapto group in the radical B can, if appropriate, be esterified by the carboxylic acid halide used, for example by the ethoxycarbonyl radical when using chloroformic acid ethyl ester.

The new compounds can be used as medicaments, for example in the form of pharmaceutical preparations which contain an effective amount of the active substance together with, or mixed with, inorganic or organic, solid or liquid, pharmaceutically usable excipients which are suitable for enteral or, preferably, parenteral administration. Thus, tablets or gelatine capsules are used, which contain the active compound together with excipients for example lactose, sucrose mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminium silicate, starches, such as maize starch, wheat starch, rice starch or arrowroot, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, and/or effervescent mixtures, or adsorbents dyestuffs, flavouring substances and sweeteners. Preferably, the pharmacologically active compounds of the present invention are used in the form of injectable preparations, for example intravenously administrable preparations, or of infusion solutions. Such solutions are, preferably, isotonic aqueous solutions or suspensions and these can be prepared before use, for example from lyophilised preparations which contain the active compound by itself or together with an excipient, for example mannitol. The pharmacological preparations can be sterilised and/or contain auxiliaries for example preservatives, stabilisers, wetting agents and/or emulsifiers, solubilising agents, salts for regulating the osmotic pressure and/or buffers. The present pharmaceutical preparations which, if desired, can contain further pharmacologically valuable materials, are produced in a manner which is in itself known, for example by means of conventional mixing, granulating, dragee-making, dissolving or lyophilising processes, and contain from about 0.1 to 100%, especially from about 1 to about 50%, of lyophilisates up to 100% of the active compound.

In the context of the present description, organic radicals described as "lower" contain up to 7, preferably up to 4, carbon atoms; acyl radicals contain up to 20, preferably up to 12, carbon atoms.

The examples which follow serve to illustrate the invention.

The following systems are used in the thin layer chromatography:

System 52 A — n-butanol/glacial acetic acid/water (67:10:23)

System 67 — n-butanol/ethanol/water (40:10:50, upper phase)

System 101 — n-butanol/pyridine/glacial acetic acid/water (38:24:8:30)

System 101A — n-butanol/pyridine/glacial acetic acid/water (42:24:4:30).

EXAMPLE 1

22.6 ml of triethylamine are added, at room temperature whilst stirring and with exclusion of atmospheric moisture, to a suspension of 32.4 g of D(−)-cephaloglycine in 300 ml of methylene chloride, a clear solution being formed. This mixture is then cooled to −10° C and a solution of 12.0 g of 2-hydroxy-pyridine-5-carboxylic acid chloride in a mixture of 50 ml of N,N-dimethylformamide and 50 ml of methylene chloride is added dropwise at −10° C in the course of 30 minutes, whilst stirring and cooling. The suspension is then diluted with 200 ml of methylene chloride, stirred for 1 hour at 0° C, then treated with 200 ml of water and with 1 N aqueous sodium bicarbonate solution until a pH value of 7.2 is obtained and mixed vigorously. The methylene chloride phase is separated off and the aqueous phase is extracted twice with ethyl acetate, then cooled in an ice bath and acidified (pH 2.5) with 1 N hydrochloric acid, whilst stirring. The product obtained is filtered off and washed successively with ethanol, methanol and ether. The material on the filter is suspended in 200 ml of water and the solid product is brought into solution by the addition of 2 N aqueous sodium bicarbonate solution (pH 7.2) and the insoluble by-product (a small amount) is filtered off. The filtrate is cooled in an ice bath and acidified (pH 2.5) with 1 N hydrochloric acid. The product obtained is filtered off, washed with a large amount of cold water and dried at 30° C/0.1 mm Hg. 7$\beta$[D(−)-$\alpha$-(2-Hydroxy-pyridine-5-carboxamido)-phenylacetamido]-cephalosporanic acid melts at 242°–245° C with decomposition. Thin layer chromatogram on silica gel: $Rf_{52}A = 0.28$, $Rf_{67} = 0.23$, $Rf_{101} = 0.50$, $Rf_{101}A = 0.42$, $[\alpha]_D^{20} = +27° \pm 1°$ (c = 1.063 in dimethylsulphoxide).

EXAMPLE 2

25.0 ml of triethylamine are added, at room temperature whilst stirring and with exclusion of atmospheric moisture, to a suspension of 14.6g of D(−)-cephaloglycine in 300 ml of methylene chloride, a clear solution being formed. This mixture is then cooled to −10° C and a solution of 5.6 g of 1,6-dihydro-6-oxo-3-pyridazinecarboxylic acid chloride in 60 ml of N,N-dimethylformamide is added dropwise at −10° C in the course of 30 minutes, whilst stirring and cooling. The suspension is then stirred for 1 hour at 0° C and for 1 hour at room temperature. The clear solution is then concentrated to half its volume on a rotary evaporator at 40° C and the product is precipitated by adding 500 ml of ether and filtered off. The material on the filter is dissolved in 100 ml of water, 2 N aqueous sodium bicarbonate solution being added until a pH value of 7.2 is reached. The solution is filtered through celite and the filtrate is covered with ethyl acetate, rendered acid (pH 2.5) at 10° C, whilst stirring and cooling in an ice bath, by adding 20%, strength phosphoric acid and extracted three times with ethyl acetate. The ethyl acetate extracts are combined, washed with twice 50 ml of sodium chloride solution, dried over sodium sulphate and freed from solvent on a rotary evaporator at 45° C. The residual 7$\beta$-[D(−)-$\alpha$-(1,6-dihydro-6-oxo-3-pyridazinecarboxamido)-phenylacetamido]-cephalosporanic acid is purified by crystallising from methanol. Melting point: 210°–212° C with decomposition. Thin layer chromatogram on silica gel: $Rf_{52}A = 0.28$, $Rf_{67} = 0.24$, $Rf_{101} = 0.52$, $RF_{101A} = 0.45$; $[\alpha]_D^{20} = +48° \pm 1°$ (c = 0.798, in dimethylsulphoxide).

EXAMPLE 3

2.8 ml of triethylamine are added, at room temperature whilst stirring and with exclusion of atmospheric moisture, to a suspension of 4.0 g of D(−)-cephaloglycine in a mixture of 20 ml of methylene chloride and 20 ml of tetrahydrofurane, a clear solution being formed. This mixture is then cooled to −10° C and a suspension of 2.2 g of 2-hydroxy-quinoline-4-carboxylic acid chloride in a mixture of 10 ml of N,N-dimethylformamide and 10 ml of methylene chloride is added dropwise at −10° C in the course of 20 minutes, whilst stirring and cooling. The reaction mixture is diluted with 15 ml of tetrahydrofurane and stirred for 1.5 hours at 0° C. The product is precipitated by adding 100 ml of ether and filtered off. The material on the filter is dissolved in 50 ml of a phosphate buffer solution of pH 7.5 and the solution is extracted twice with ethyl acetate. The aqueous phase is separated off, covered with ethyl acetate, rendered acid (pH 2.5) at 10° C, whilst stirring and cooling in an ice bath, by adding 20% strength phosphoric acid and extracted three times with ethyl acetate. The ethyl acetate extracts are combined, washed twice with sodium chloride solution, dried over sodium sulphate and freed from solvent on a rotary evaporator at 45° C. The residual product is purified by crystallising from methanol. 7$\beta$-[D(−)-$\alpha$-(2-Hydroxyquinoline-4-carboxamido-phenylacetamido]-cephalosporanic acid melts at 218°–221° C with decomposition. Thin layer chromatogram on silica gel: $Rf_{52A} = 0.35$, $Rf_{67} = 0.32$, $Rf_{101} = 0.57$, $Rf_{101A} = 0.48$; $[\alpha]_D^{20} = +27° \pm 1°$(C = 1.008, in dimethylsulphoxide).

EXAMPLE 4

4.20 ml of triethylamine are added, at room temperature whilst stirring and with exclusion of atmospheric moisture, to a suspension of 4.05 g of D(−)-cephaloglycine in 30 ml of methylene chloride, a clear solution being formed. This mixture is then cooled to −10° C and a solution of 2.31 g of 2,6-dichloro-pyridine-4-carboxylic acid chloride in 20 ml of methylene chloride is added dropwise at −10° C in the course of 15 minutes, whilst stirring and cooling. Thereafter, the suspension is stirred for 1.5 hours at −10° C, then diluted with 200 ml of ethyl acetate and extracted with 100 ml of a phosphate buffer solution of pH 7.5. The aqueous phase is separated off, extracted twice with ethyl acetate (neutral extract), then covered with ethyl acetate, rendered acid (pH 2.5) at 10° C, whilst stirring and cooling in an ice bath, by adding 20% strength phosphoric acid and extracted three times with ethyl acetate. The last three ethyl acetate extracts are combined, washed twice with sodium chloride solution and dried over sodium sulphate and the solvent is evaporated on a rotary evaporator at 45° C. The residual product is purified by crystallising from methanol. 7$\beta$-[D(−)-$\alpha$-(2,6-Dichloro-pyridine-4-carboxamido-phenylacetamido]-cephalosporanic acid melts at 193°–195° C with decomposition. Thin layer chromatogram on silica gel: $Rf_{52}A = 0.44$, $Rf_{67} = 0.50$, $Rf_{101} = 0.59$, $Rf_{101A} = 0.55$. $[\alpha]_D^{20} = +26° \pm 1°$ (c = 1.063 in dimethylsulphoxide).

EXAMPLE 5

21.0 ml of triethylamine are added, at room temperature whilst stirring and with exclusion of atmospheric moisture, to a suspension of 20.0 g of D(−)-cephaloglycine in a mixture of 300 ml of methylene chloride and 600 ml of tetrahydrofurane, a clear solution being formed. This mixture is then cooled to 0° C and a solution of 11.0 g of 3-methylmercapto-5-hydroxy-1,2,4-triazine-6-carboxylic acid chloride in a mixture of 40 ml of N,N-dimethylformamide and 40 ml of tetrahydrofurane is added dropwise at 0° C in the course of 30 minutes, whilst stirring and cooling. The suspension is then stirred for 1 hour at room temperature and then concentrated to a volume of about 100 ml of a rotary evaporator (waterpump vacuum) at 45° C. The product is precipitated by adding 400 ml of ether, filtered off and washed with water. The material on the filter is worked up as in Example 3. After recrystallisation from ethyl acetate, 7β-[D(−)-α-(3-methylmercapto-5-hydroxy-1,2,4-triazine-6-carboxamido)-phenylacetamido]-cephalosporanic acid melts at 235°–240° C with decomposition. Thin layer chromatogram on silica gel: $Rf_{52A} = 0.28$, $Rf_{67} = 0.25$, $Rf_{101} = 0.50$, $Rf_{101A} = 0.41$. $[\alpha]_D^{20} = +42° \pm 1°$ (c = 0.994 in dimethylsulphoxide).

EXAMPLE 6

13.0 ml of triethylamine are added, at room temperature, whilst stirring and with exclusion of atmospheric moisture, to a suspension of 12.5 g of D(−)-cephaloglycine in a mixture of 200 ml of methylene chloride and 300 ml of tetrahydrofurane, a clear solution being formed. This mixture is then cooled to 0° C and a solution of 7.65 g of 3,5-dioxo-2,3,4,5-tetrahydro-1,2,4-triazine-6-carboxylic acid chloride into a mixture of 40 ml of N,N-dimethylformamide and 40 ml of tetrahydrofurane is added dropwise at 0° C in the course of 30 minutes, whilst stirring and cooling. The suspension is then stirred for 1 hour at room temperature and then concentrated to a volume of about 100 ml on a rotary evaporator (waterpump vacuum) at 45° C. The product is precipitated by adding 400 ml of ether, filtered off and washed with ether. The material on the filter is worked up as in Example 3. 7β−[D(−)-α-(3,5-Dioxo-2,3,4,5-tetrahydro-1,2,4-triazine-6-carboxamido)-phenylacetamido]-cephalosporanic acid crystallise from ethyl acetate. Melting point: 153°–158° C with decomposition. Thin layer chromatogram on silica gel: $Rf_{52A} = 0.32$, $Rf_{67} = 0.20$, $Rf_{101} = 0.52$, $Rf_{101}A = 0.48$. $[\alpha]_D^{20} = +31° \pm 1°$ (c = 1.089 in dimethylsulphoxide).

EXAMPLE 7

5.88 ml of triethylamine are added, at room temperature whilst stirring and with exclusion of atmospheric moisture, to a suspension of 2.55 g of 7β-[D(−)-α-amino-phenylacetamido]-3-methoxy-ceph-3-em-4-carboxylic acid dihydrate in 200 ml of absolute dimethylformamide, a clear solution being formed. This mixture is then cooled to 0° C and a solution of 1.85 g of 3,5-dioxo-2,3,4,5-tetrahydro-1,2,4-triazine-6-carboxylic acid chloride in a mixture of 7 ml of N,N-dimethylformamide and 12 ml of tetrahydrofurane is added dropwise at 0° C in the course of 10 minutes, whilst stirring and cooling. The suspension is then stirred for 30 minutes at 0° C and for 2 hours at room temperature. The product is precipitated by adding 1 l of ether, filtered off and washed with ether. The material on the filter is dissolved in 100 ml of a phosphate buffer solution of pH 7.5 and the solution is extracted twice with ethyl acetate. The aqueous phase is separated off, covered with ethyl acetate, rendered acid (pH 2.5) at 10° C, whilst stirring and cooling in an ice bath, by adding 20% strength phosphoric acid and extracted three times with ethyl acetate. The ethyl acetate extracts are combined, washed three times with sodium chloride solution and dried over sodium sulphate and the solvent is evaporated on a rotary evaporator. The residual product is purified by dissolving in acetone and precipitating with ethyl acetate. 7β-[D(−)-α-(3,5-Dioxo-2,3,4,5-tetrahydro-1,2,4-triazine-6-carboxamido0-phenylacetamido]-3-methoxy-ceph-3-em-4-carboxylic acid melts at 183°–185° C with decomposition. Thin layer chromtogram on silica gel: $Rf_{52}A$: 0.33, $[\alpha]_D = +78° \pm 1°$ (c = 1.0, methanol).

EXAMPLE 8

A solution of 1.90 g of 2-amino-5-mercapto-1,3,4-thiadiazole (prepared according to the method of J. Sandström, Acta chem. Scand. 15, 1295 (1961)) in 20 ml of 0.5 N aqueous sodium bicarbonate solution is added to a clear solution of 7.05 g of 7β-[D(−)-α-(3,5-dioxo-2,3,4,5-tetrahydro-1,2,4-triazine-6-carboxamido)-phenylacetamido]-cephalosporanic acid (prepared as in Example 6) in a mixture of 30 ml of water and 70 ml of 0.5 N aqueous sodium bicarbonate solution and the reaction mixture is stirred for 20 hours at 60° C in a nitrogen atmosphere. At the start of the reaction the pH value of the reaction mixture rises and is brought back to a pH value of 7.5 to 7.6 by the occasional dropwise addition of 0.1 N hydrochloric acid. After the reaction time has elapsed, the reaction mixture is cooled to room temperature and extracted twice with ethyl acetate. The aqueous phase is separated off, cooled in an ice bath and acidified (pH 3.0) with 20% strength phosphoric acid and the solid product obtained is filtered off and washed with water. The material on the filter is then suspended in 1 liter of ethyl acetate and the suspension is stirred for 5 minutes at room temperature and filtered. The material on the filter is then introduced into 1 liter of a mixture of methanol/tetrahydrofurane (1:1) and the mixture is stirred for 10 minutes at room temperature. The insoluble fraction is filtered off and the filtrate is evaporated on a rotary evaporator (waterpump vacuum) at 45° C. The residual 7β-[D(-)-α-(3,5-dioxo-2,3,4,5-tetrahydro-1,2,4-triazine-6-carboxamido)-phenylacetamido]-3-[(2-amino-1,3,4-thiadiazol-5-ylthio)methyl]-ceph-3-em-4-carboxylic acid crystallises on mixing with ethyl acetate. Melting point: 255°–260° C with decomposition. Thin layer chromatogram on silica gel: $Rf_{52A} = 0.32$, $Rf_{67} = 0.20$, $Rf_{101} = 0.52$, $Rf_{101A} = 0.48$. $[\alpha]_D^{20} = -64° \pm 1°$ (c = 1.036 in dimethylsulphoxide).

EXAMPLE 9

A solution of 0.93 g of 2-(β-carboxy-propionylamido)-5-mercapto-1,3,4-thiadiazole in 11 ml of 0.5 N aqueous sodium bicarbonate solution is added to a clear solution of 2.0 g of 7β-[D(-)-α-(3,5-dioxo-2,3,4,5-tetrahydro-1,2,4-triazine-6-carboxamido)-phenylacetamido]-cephalosporanic acid (prepared as in Example 6) in a mixture of 10 ml of water and 20 ml of 0.5 N aqueous sodium bicarbonate solution and the reaction mixture is stirred for 20 hours at 60° C in a nitrogen atmosphere. At the start of the reaction the pH value of the reaction mixture rises and is brought back to a pH value of 7.5 to 7.6 by the occasional dropwise addition of 0.1 N hydrochloric acid. After the reaction time has elapsed, the reaction mixture is cooled to room temperature and extracted twice with ethyl acetate. The aqueous phase is separated off, cooled in an ice bath and acidified (pH 2.5) with 20% strength phosphoric acid and the solid product obtained is filtered off and washed with water. The material on the filter is dissolved in a mixture of 20 ml of methanol and 20 ml of tetrahydrofurane and the solution is concentrated to a volume of about 10 ml on a rotary evaporator (waterpump vacuum) at 45° C and ethyl acetate is then added, whereupon the product crystallises. After recrystallisation from ethyl acetate, 7β-[D(−)-α-(3,5-dioxo-2,3,4,5-tetrahydro-1,2,4-triazine-6-carboxamido)-phenylacetamido]-3-[(2-(β-carboxy-propionylamido)-1,3,4-thiadiazol-5-ylthio)-methyl]ceph-3-em-4-carboxylic acid melts at 226°–227° C with decomposition. Thin layer chromatogram on silica gel: $Rf_{52} = 0.26$, $Rf_{67} = 0.05$, $Rf_{101A} = 0.36$. $[\alpha]_D^{20} = -50° \pm 1°$ (c = 1.234 in dimethylsulphoxide).

Preparation of the Starting Material 23 ml of triethylamine are added to a solution of 20.0 g of 2-amino-5-mercapto-1,3,4-thiadiazole (prepared according to the method of J. Sandström, Acta Chem. Scand. 15, 1295 (1961)) in 600 ml of dioxane, a suspension being formed. This suspension is cooled to 10° C using an ice bath, and 25.0 g of succinic acid monomethyl ester chloride are added dropwise at 10°–13° C in the course of 30 minutes, whilst stirring vigorously, and the reaction mixture is then stirred for 20 hours at room temperature. The precipitate is then filtered off, the material on the filter is washed with a little dioxane and the filtrate is evaporated to dryness on a rotary evaporator (high vacuum) at 40° C. The residual solid product is mixed with a little water and filtered off. 28.0 g of the crude product are suspended in 840 ml of 1 N sodium bicarbonate solution, the suspension is stirred vigorously for 5 minutes at room temperature, the insoluble fraction is filtered off and the aqueous filtrate is cooled to 3° C in an ice bath and is rendered acid (pH 2.5) by the dropwise addition of 2 N hydrochloric acid. The product obtained is filtered off and washed with cold water. After recrystallisation from hot water, 2-(β-carbomethoxypropionylamido)-5-mercapto-1,3,4-thiadiazole melts at 210°–212° C with decomposition. Thin layer chromatogram on silica gel (running agent: chloroform/ethyl acetate/glacial acetic acid (66:33:0.25)): Rf = 0.17.

A solution of 17.0 g of 2-(β-carbomethoxypropionylamido)-5-mercapto-1,3,4-thiadiazole in a mixture of 130 ml of water and 155 ml of 1 N aqueous sodium hydroxide solution is stirred for 20 hours at room temperature. Therefter the yellow solution is filtered and the filtrate is then cooled to 5° C in an ice bath and rendered acid (pH 2.0) by the dropwise addition of dilute hydrochloric acid (1:1). The product obtained is filtered off and washed with cold water. After recrystallisation from hot water, 2-(β-carboxypropionylamido)-5-mercapto-1,3,4-thiadiazole melts at 225°–230° C with decomposition. Thin layer chromatogram on silica gel (running agent: chloroform/ethyl acetate/glacial acetic acid (66:33:1.5)): Rf = 0.15.

EXAMPLE 10

In accordance with the process of Example 8, 7β-[D(−)-α-(3,5-dioxo-2,3,4,5-tetrahydro-1,2,4-triazine-6-carboxamido)-phenylacetamido]-3-[(1-methyl-1H-tetrazol-5-ylthio)methyl]-ceph-3-em-4-carboxylic acid is obtained by reacting 5.44 g of 7β-[D(−)-α-(3,5-dioxo-2,3,4,5-tetrahydro-1,2,4-triazine-6-carboxamido)-phenylacetamido]-cephalosporanic acid (prepared as in Example 6) with 1.30 g of 5-mercapto-1-methyl-tetrazole in water in the presence of sodium bicarbonate.

EXAMPLE 11

In accordance with the process of Example 7, 7β-[D(−)-α-(3,5-dioxo-2,3,4,5-tetrahydro-1,2,4-triazine-6-carboxamido)-phenylacetamido]-3-[(1H-1,2,3-triazol-5-ylthio)methyl]-ceph-3-em-4-carboxylic acid is obtained by reacting 6.00 g of 7β-[D(−)-α-(3,5-dioxo-2,3,4,5-tetrahydro-1,2,4-triazine-6-carboxamido)-phenylacetamido]-cephalosporanic acid (prepared as in Example 6) with 1.25 g of 5-mercapto-1H-1,2,3-triazole (prepared in accordance with the method of J. Goerdeler and G. Gnad, Chem. Ber. 99, 1618 (1966)) in water in the presence of sodium bicarbonate.

EXAMPLE 12

6 ml of a 40% strength aqueous mercury perchlorate solution are added to a solution of 1.5 g of the sodium salt of 3-benzoylthiomethyl-7β-[D(−)-α-(3,5-dioxo-2,3,4,5-tetrahydro-1,2,4-triazine-6-carboxamido)-phenylacetamido]-ceph-3-cm-4-carboxylic acid and 3.2 g of isonicotinic acid amide in 15 ml of water and 15 ml of dioxane and the reaction mixture is stirred vigorously for 1 hour at 45° C in a nitrogen atmosphere. The suspension is then cooled to 0° C, 4 ml of thiobenzoic acid are added dropwise, the mixture is stirred for 5 minutes at +10° C and the mercury salt obtained is removed by filtering through celite and the material on the filter is washed with a 1:1 mixture of water and dioxane. The filtrate is washed successively twice with petroleum ether, twice with, in each case, 100 ml of a 10% strength solution of "Amberlite" LA-2 in petroleum ether and finally with petroleum ether. The aqueous phase is separated off and evaporated to dryness on a rotary evaporator (high vacuum) at 45° C. The solid residue is mixed well with a mixture of methanol/ethanol/diethyl ether (1:1:1) and the insoluble 7β-[D(−)-α-(3,5-dioxo-2,3,4,5-tetrahydro-1,2,4-triazine-6-carboxamido)-phenylacetamido]-3-[1-(4-carbamoyl-pyridiniomethyl)]-ceph-3-em-4-carboxylate is filtered off and washed with the above solvent mixture.

Preparation of the Starting Material

A solution of 10.0 g of 7β-[D(−)-α-(3,5-dioxo-2,3,4,5-tetrahydro-1,2,4-triazine-6-carboxamido)-phenylacetamido]-cephalosporanic acid (prepared as in Example 6) in 20 ml of water and 46 ml of 1 N sodium bicarbonate solution is added to a solution of 9.0 g of thiobenzoic acid and 6.05 g of solid sodium bicarbonate in 50 ml of water and the reaction mixture is stirred for 20 hours at 50°–55° C in a nitrogen atmosphere. At the start of the reaction the pH value of the reaction mixture rises and is brought back to a pH value of 7.6 to 7.7 by the occasional dropwise addition of 0.1 N hydrochloric acid. After the reaction time has elapsed, the suspension is cooled to 10° C and the sodium salt of 3-benzoylthiomethyl-7β-[D(−)-α-(3,5-dioxo-2,3,4,5-tetrahydro-1,2,4-triazine-6-carboxamido)- phenylacetamido]-ceph-3-em-4-carboxylic acid, which is obtained, is filtered off and washed with a little cold water. Melting point: 215°-220° C with decomposition. Thin layer chromatogram on silica gel: $Rf_{52A} = 0.41$; $Rf_{101A} = 0.53$.

EXAMPLE 13

Dry powders of phials, containing 0.6 g of the sodium salt of 7β-[D(−)-α-(3,5-dioxo-2,3,4,5-tetrahydro-1,2,4-triazine-6-carboxamido)-phenylacetamido]-cephalosporanic acid are prepared as follows:

| Composition (for 1 ampoule or phial) | |
|---|---|
| Sodium salt of 7β-[D(-)-α-(3,5-dioxo-2,3,4,5-tetrahydro-1,2,4-triazine-6-carboxamido)-phenylacetamido]-cephalosporanic acid | 0.6 g |
| Mannitol | 0.06 g |

A sterile aqueous solution of the sodium salt of 7β-[D(−)-α-(3,5-dioxo-2,3,4,5-tetrahydro-1,2,4-triazine-6-carboxamido)-phenylacetamido]-cephalosporanic acid and of the mannitol is subjected to freeze-drying in 5 ml ampoules or 5 ml phials under aseptic conditions and the ampoules or phials are sealed and tested.

We claim:

1. A compound of the formula

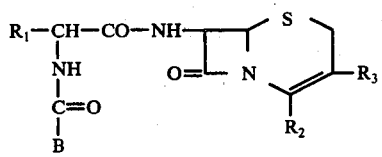

(I)

wherein $R_1$ denotes phenyl, thienyl, furyl, 1,4-cyclohexadienyl or phenyl substituted by hydroxy, $R_2$ represents a free carboxyl group, $R_3$ denotes hydrogen, lower alkanoyloxymethyl, benzoylthiomethyl, pyridiniomethyl, pyridiniomethyl substituted by lower alkyl, halogen, trifluoromethyl, hydroxyl, carboxyl and lower alkoxy carbonyl, and B denotes one of the groups $B_5$ or $B_6$, of which $B_5$ represents the formula

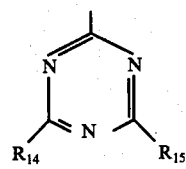

(B$_5$)

wherein $R_{14}$ and $R_{15}$ independently of one another denote hydrogen, halogen, a free hydroxyl or mercapto group, a lower alkoxy or a lower alkyl mercapto group or a lower alkoxy carbonyloxy or a lower alkoxy carbonyl mercapto group, or mono- or di-lower alkylated amino group, a lower alkanoylated amino group, or ureido group
or of which $B_6$ represents the formula

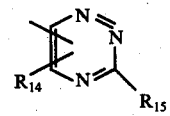

(B$_6$)

wherein $R_{14}$ and $R_{15}$ have the meaning mentioned under formula (B$_5$), the substituent $R_{14}$ preferably occupying the 5-position of the as-triazine ring, a tautomer, or a salt thereof.

2. A compound of the formula I according to claim 1, wherein $R_1$ and $R_2$ have the meaning mentioned under formula I, $R_3$ denotes lower alkanoyloxymethyl, benzoylthiomethyl, pyridiniomethyl, pyridiniomethyl substituted by lower alkyl, halogen, trifluoromethyl, hydroxyl, carboxyl, and lower alkoxy carbonyl, the group B denotes 1,3,4-triazine di-substituted by hydroxyl and/or methylmercapto, a tautomer thereof, or a salt thereof.

3. A compound according to claim 1 which is 7β-[D(−)-α-(3-methylmercapto-5-hydroxy-1,2,4-triazine-6-carboxamido)-phenylacetamido]-cephalosporanic acid or a pharmaceutically acceptable salt thereof.

4. A compound according to claim 1 which is 7β-[D(−)-α-(3,5-dioxo-2,3,4,5-tetrahydro-1,2,4-triazine-6-carboxamido)-phenylacetamido]-cephalosporanic acid or a pharmaceutically acceptable salt thereof.

5. A pharmaceutical preparation for combatting bacteria which comprises an antibacterially effective amount of a compound of claim 1 and a pharmaceutically usable excipient.

6. A pharmaceutical preparation according to claim 5, wherein the active compound is 7β-[D(−)-α-(3,5-dioxo-2,3,4,5-tetrahydro-1,2,4-triazine-6-carboxamido)-phenylacetamido]-cephalosporanic acid or a pharmaceutically acceptable salt thereof.

* * * * *